(12) United States Patent
Jiang et al.

(10) Patent No.: US 7,224,766 B2
(45) Date of Patent: May 29, 2007

(54) CT DETECTOR ARRAY HAVING NON-PIXELATED SCINTILLATOR ARRAY

(75) Inventors: Haochuan Jiang, Brookfield, WI (US); David M. Hoffman, New Berlin, WI (US); James S. Vartuli, Rexford, NY (US)

(73) Assignee: General Electric Company, Schenectady, NY (US)

( * ) Notice: Subject to any disclaimer, the term of this patent is extended or adjusted under 35 U.S.C. 154(b) by 272 days.

(21) Appl. No.: 11/029,612

(22) Filed: Jan. 4, 2005

(65) Prior Publication Data

US 2005/0133725 A1 Jun. 23, 2005

Related U.S. Application Data

(62) Division of application No. 10/249,694, filed on Apr. 30, 2003, now Pat. No. 7,054,408.

(51) Int. Cl.
| | |
|---|---|
| H05G 1/60 | (2006.01) |
| G01T 1/20 | (2006.01) |
| C09K 11/08 | (2006.01) |
| C09K 11/77 | (2006.01) |

(52) U.S. Cl. .................. 378/19; 250/367; 250/370.09; 250/370.11; 252/301.4 R

(58) Field of Classification Search ............... 378/19, 378/98.8; 250/367, 368, 370.09, 370.11; 117/81–83; 252/301.4 R
See application file for complete search history.

(56) References Cited

U.S. PATENT DOCUMENTS

| 4,096,381 A | 6/1978 | Brown, Sr. ............ 250/214 VT |
| 4,179,100 A | 12/1979 | Sashin et al. ............ 250/370.09 |
| 4,194,914 A * | 3/1980 | Moriya et al. ............ 106/18.14 |
| 4,365,155 A | 12/1982 | Oi et al. |
| 4,421,671 A | 12/1983 | Cusano et al. |
| 4,473,513 A | 9/1984 | Cusano et al. |
| 4,525,628 A | 6/1985 | DiBianca et al. |
| 4,783,596 A | 11/1988 | Riedner et al. |
| 5,484,750 A * | 1/1996 | Greskovich et al. .......... 501/86 |

(Continued)

OTHER PUBLICATIONS

Valery I. Chani et al., Melt Growth of (Tb,Lu)3 Al5 O12 Mixed Garnet Fiber Crystals, Journal of Crystal Growth, 2000, pp. 469-475, vol. 212, Publisher: Elsevier Science B.V., Published in: US.

Primary Examiner—Allen C. Ho
(74) Attorney, Agent, or Firm—Ziolkowski Patent Solutions Group, SC; Michael A. Della Penna; Carl B. Horton

(57) ABSTRACT

The present invention is a directed to a non-pixelated scintillator array for a CT detector as well as an apparatus and method of manufacturing same. The scintillator array is comprised of a number of ceramic fibers or single crystal fibers that are aligned in parallel with respect to one another. As a result, the pack has very high dose efficiency. Furthermore, each fiber is designed to direct light out to a photodiode with very low scattering loss. The fiber size (cross-sectional diameter) may be controlled such that smaller fibers may be fabricated for higher resolution applications. Moreover, because the fiber size can be controlled to be consistent throughout the scintillator array and the fibers are aligned in parallel with one another, the scintillator array, as a whole, also is uniform. Therefore, precise alignment with the photodiode array or the collimator assembly is not necessary.

20 Claims, 8 Drawing Sheets

U.S. PATENT DOCUMENTS

| | | |
|---|---|---|
| 5,521,387 A | 5/1996 | Riedner et al. ............. 250/367 |
| 5,583,908 A | 12/1996 | Antich et al. ................. 378/65 |
| 6,210,605 B1 * | 4/2001 | Srivastava et al. .... 252/301.4 R |
| 6,245,184 B1 * | 6/2001 | Riedner et al. ............. 156/247 |
| 6,298,113 B1 | 10/2001 | Duclos et al. ................ 378/19 |
| 6,302,959 B2 * | 10/2001 | Srivastava et al. ............ 117/81 |
| 6,328,027 B1 * | 12/2001 | Persyk et al. ................ 125/21 |
| 6,340,436 B1 * | 1/2002 | Yamada et al. ............ 385/115 |
| 6,344,649 B2 * | 2/2002 | Riedner et al. ............. 250/367 |
| 6,384,400 B1 | 5/2002 | Albagli et al. ........ 250/214 VT |
| 6,458,295 B1 | 10/2002 | Yamada et al. ....... 252/301.4 R |
| 6,480,562 B2 * | 11/2002 | Jiang et al. ................... 378/19 |
| 6,495,845 B1 * | 12/2002 | Tsunota et al. ........... 250/505.1 |
| 6,630,077 B2 | 10/2003 | Shiang et al. ......... 252/301.4 R |
| 6,793,848 B2 * | 9/2004 | Vartuli et al. ......... 252/301.4 R |

\* cited by examiner

CT DETECTOR ARRAY HAVING NON-PIXELATED SCINTILLATOR ARRAY

The present application is a divisional and claims priority of U.S. patent application Ser. No. 10/249,694 filed Apr. 30, 2003, now U.S. Pat. No. 7,054,408 B2, the disclosure of which is incorporated herein.

BACKGROUND OF INVENTION

The present invention relates generally to diagnostic imaging and, more particularly, to a non-pixelated scintillator array incorporated into a detector array for a CT imaging system. More particularly, the invention relates to a scintillator array formed of a plurality of ceramic or single crystal fibers as well as a method and apparatus for forming the ceramic or single crystal scintillator fibers.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator illuminates and thereby discharges light energy to a photodiode adjacent thereto. Each photodiode detects the light energy and generates a corresponding electrical signal. The outputs of the photodiodes are then transmitted to the data processing system for image reconstruction.

Each photodiode of the photodiode array is aligned to correspond with a scintillator of the scintillator array. Known CT detectors have pixelated scintillator arrays that, ideally, are dimensionally equivalent throughout the scintillator array. Because there is a one-to-one relationship between photodiode and scintillator, it is imperative that each scintillator be precisely aligned with each photodiode. This precision becomes increasingly important as a result of the exactness required when developing reflector elements between the scintillator pixels and coupling a single-piece or multi-piece collimator assembly to the scintillator array. Because it is extremely difficult to form a small channel or groove between each pixelated structure, thicker reflector plates or walls are used to separate each of the scintillators. This leads to decreased surface area of the active scintillator and reduced quantum detection efficiency or dose usage. Reflector protecting material, such as tungsten, absorbs x-rays thereby increasing the radiation dosage required for data acquisition. Additionally, the specification for misalignment is usually very limited to maintain acceptable image quality. Further, high resolution applications require small scintillation cells which are difficult to form into a pixelated layout.

A number of fabrication techniques have been developed to achieve the necessary precision. These techniques include developing a ceramic wafer using well-known semiconductor fabrication processes and, through precisely controlled dicing and grinding, forming scintillator arrays or packs. Using accurate dicing and grinding processing and equipment, the packs may be processed to develop a series of pixelated structures. As noted above, however, the pixelated structures must be exactly aligned so that misalignment between the scintillators, photodiodes, and the collimator assembly during subsequent fabrication is minimized. Misalignment, however minor, can contribute to cross-talk, x-ray generated noise, and radiation damage to the photodiode array. If the misalignment is too severe, the scintillator pack must be discarded thereby increasing fabrication costs, labor, time, and waste.

Therefore, it would be desirable to design an apparatus and method of fabricating a scintillator array for high resolution CT imaging with reduced sensitivities to alignment of the scintillator array with the photodiode array and/or collimator assembly.

BRIEF DESCRIPTION OF INVENTION

The present invention is a directed to non-pixelated scintillator array for a CT detector as well as an apparatus and method of manufacturing same that overcomes the aforementioned drawbacks. The scintillator array is comprised of a number of ceramic or single crystal fibers that are aligned in parallel with respect to one another. The fibers may have uniform or non-uniform cross-sectional diameters. The fibers are arranged in a scintillator array or pack that has relatively little reflector material disposed between adjacent fibers. As a result, the pack has very high dose efficiency. Furthermore, each fiber is designed to direct light out to a photodiode with very low scattering loss. In this regard, the scintillator array has a relatively high light output but low cross-talk. The fiber size (cross-sectional diameter) may be controlled such that smaller fibers may be fabricated for higher resolution applications. Moreover, because the fiber size can be controlled to be consistent throughout the scintillator array and the fibers are aligned in parallel with one another, the scintillator array, as a whole, also is uniform. Therefore, precise alignment with the photodiode array or the collimator assembly is not necessary.

Therefore, in accordance with one aspect of the present invention, a CT detector array includes a plurality of collimator elements configured to collimate x-rays projected thereat as well as a non-pixelated scintillator pack formed of a material that illuminates upon reception of x-rays. The CT detector array further includes a photodiode array optically coupled to the non-pixelated scintillator pack and configured to detect illumination from the scintillator pack and output electrical signals responsive thereto.

In accordance with another aspect of the present invention, a CT detector array comprising a non-pixelated array of scintillation elements configured to illuminate upon the reception of high frequency electromagnetic energy and coupled to an array of light detection elements configured to detect illumination of the array of scintillation elements and output a plurality of electrical signals generally indicative of high frequency electromagnetic energy received by the array of scintillation elements is provided. The detector array is formed by developing the plurality of single crystal fibers of scintillation material and casting the plurality of crystal fibers with an adhesive material. The detector array is further formed by curing the plurality of crystal fibers in adhesive material to form a cured pack and cutting the cured pack to a specified dimension.

According to another aspect of the present invention, a method of manufacturing a CT detector array having a non-pixelated scintillator array includes the steps of developing a material base from which scintillators may be grown and pulling a rod of scintillating material from a material base. The method further includes cutting the rod to form a plurality of scintillator fibers and aligning the plurality of scintillator fibers into a scintillator bundle. The scintillator bundle is then sliced into a number of scintillator packs whereupon a reflector coating is applied to the number of scintillator packs.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
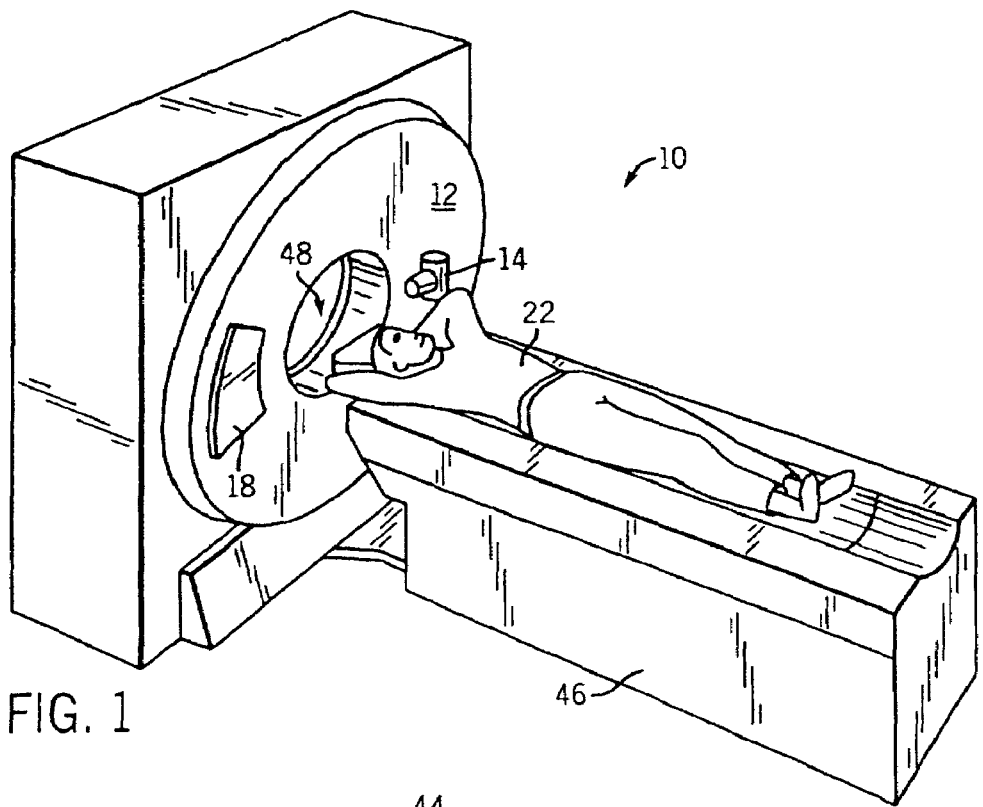
FIG. 1 is a pictorial view of a CT imaging system.
Figure 2:
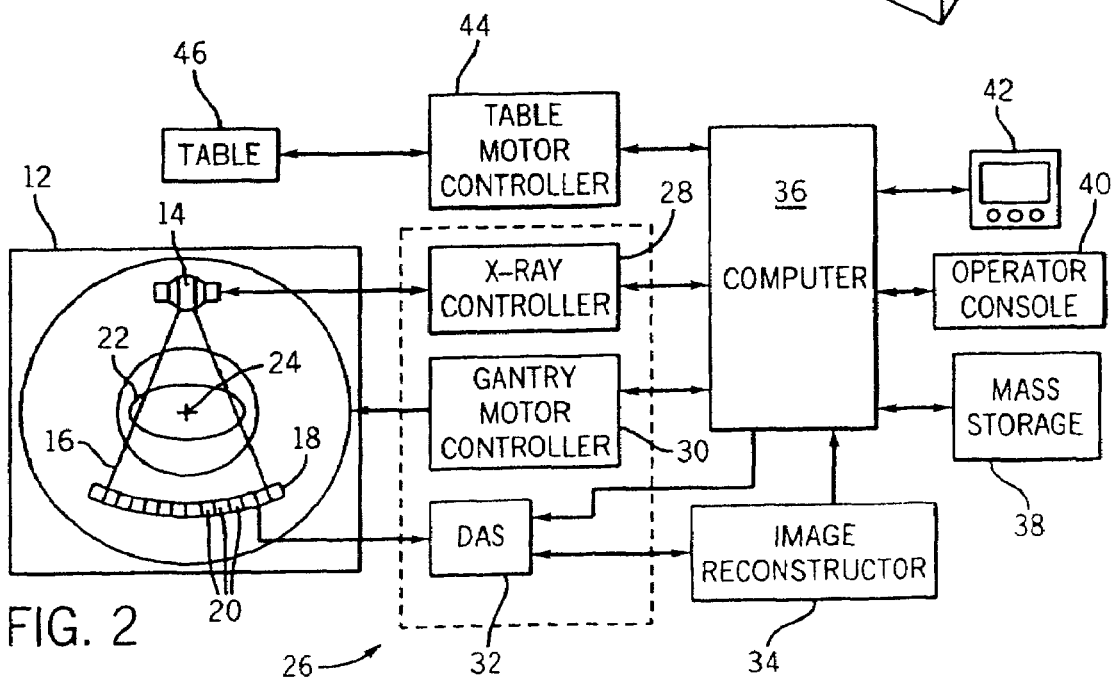
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figure 3:
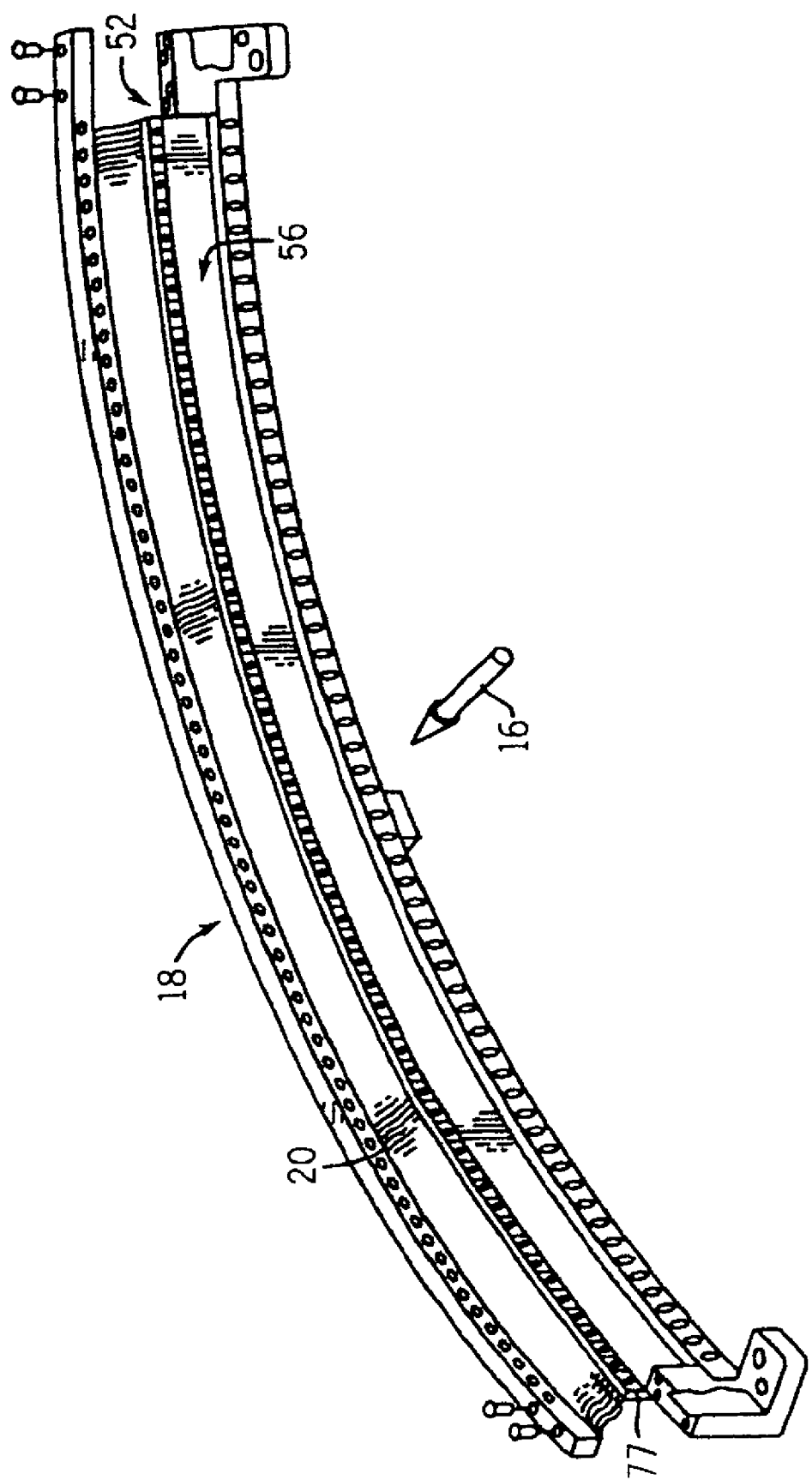
FIG. 3 is a perspective view of one embodiment of a CT system detector array.
Figure 4:
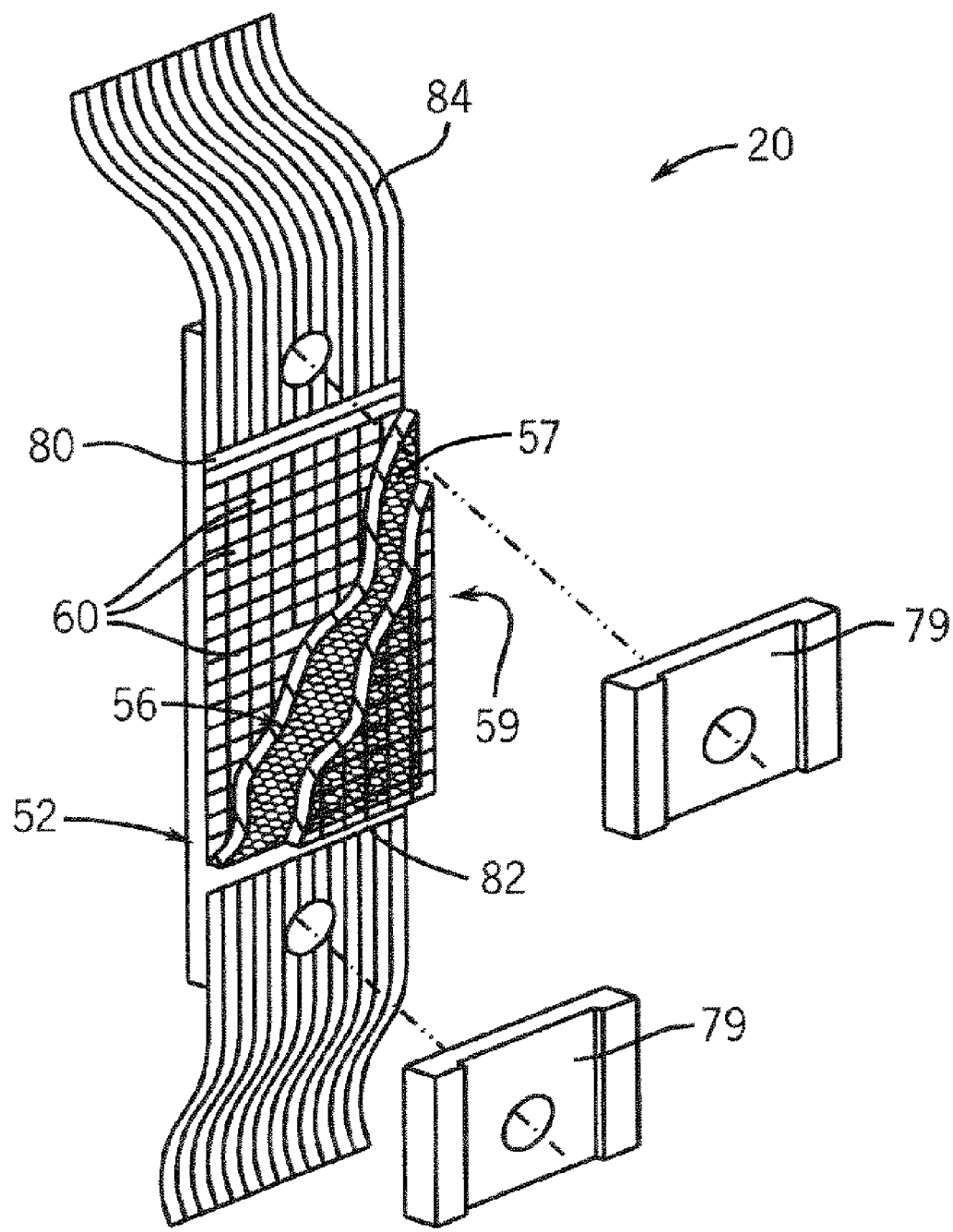
FIG. 4 is a perspective view of one embodiment of a detector.

As shown in FIGS. 3 and 4, detector array 18 includes a plurality of single scintillator fibers 57 forming a scintillator array 56. A collimator assembly 59 is positioned above scintillator array 56 to collimate x-ray beams 16 before such beams impinge upon scintillator array 56. In one embodiment, the collimator assembly is integrally formed with a top or x-ray reception surface of the scintillator array.

In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a thin reflector layer (not shown) may be interposed between each scintillator fiber 57 to reduce light scattering from adjacent scintillators. Each detector 20 is secured to a detector frame 77, FIG. 3, by mounting brackets 79.

Switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Figure 5:
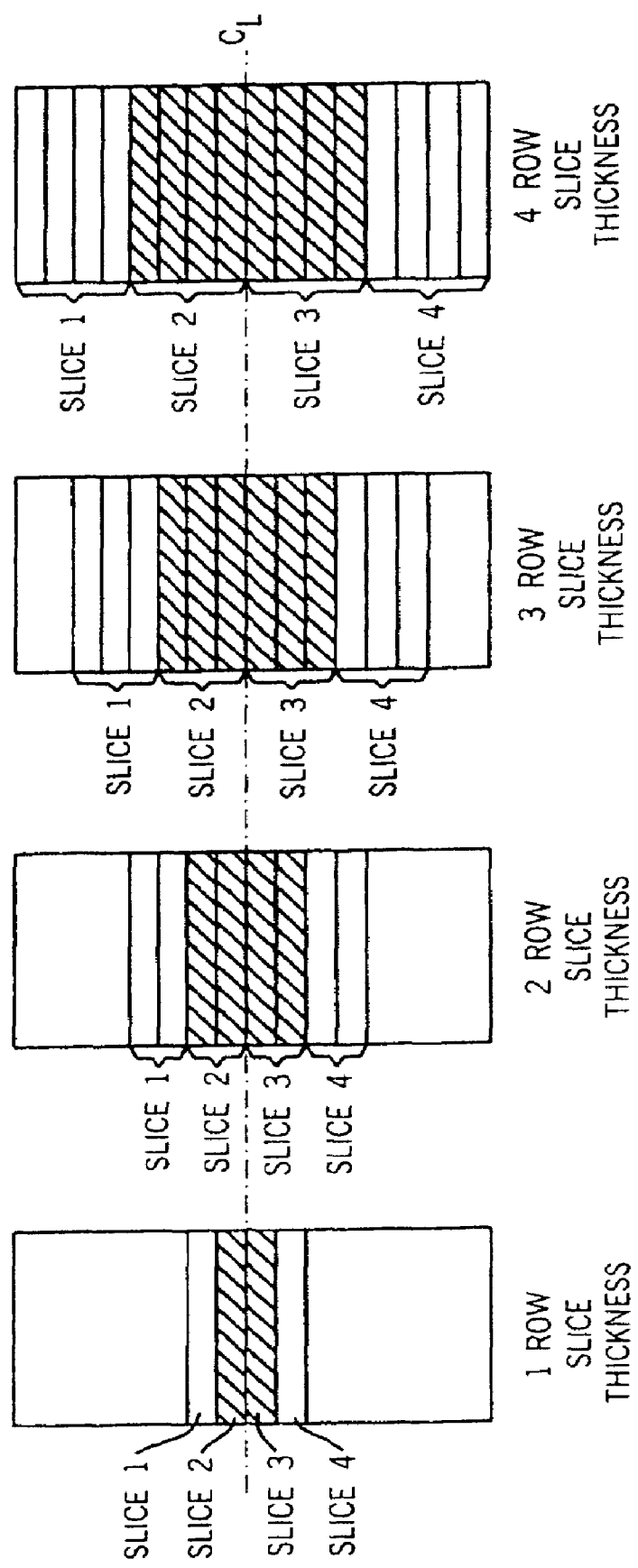
FIG. 5 is illustrative of various configurations of the detector in FIG. 4 in a four-slice mode.

As shown in FIG. 5, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

Figure 6:
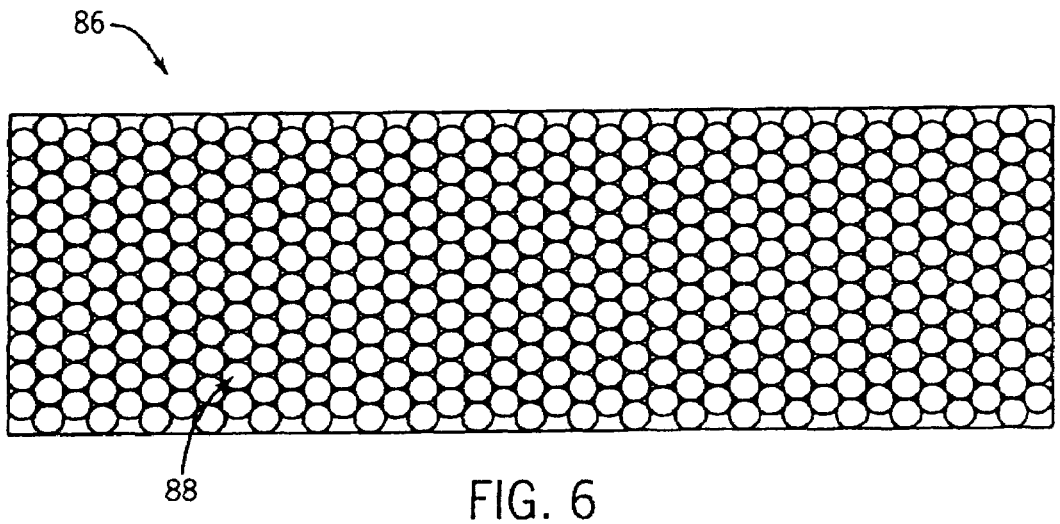
FIG. 6 is a top view of a scintillator pack in accordance with the present invention.

Referring now to FIG. 6, a top view of a scintillator pack constructed in accordance with the present invention is shown. The scintillator pack 86 is defined by a plurality of single crystal or ceramic fibers 88 that dimensionally populate the pack. As will be described in greater detail below, a number of techniques may be used to develop fibers 88. Each of the scintillator fibers are cylindrical in shape are constructed to focus light generated upon the reception of x-rays or y-rays toward a photodiode, as discussed with respect to FIGS. 3-4. In one embodiment, the scintillator fibers have a uniform cross-sectional diameter. As such, there is uniformity in scintillator size throughout the pack 86. Some of the advantages of this uniformity will be explained in greater detail below. In another embodiment, the fibers may be developed and arranged such that there are differences in cross-sectional diameter within the pack. This non-uniformity may be suitable or preferred for some applications. Moreover, incorporation on non-uniform elements into pack 86 may allow for more fibers to fit within the pack. The more scintillation elements or fibers fit within the pack increases packing efficiency which also improves dose efficiency. That is, increasing the number of scintillation cells within a fixed space reduces the amount of non-scintillation surface area within the fixed space. Accordingly, the more scintillation material used within the fixed space increases the number of x-rays or y-rays detected within that fixed space. As will be described in greater detail below, the present invention allow for formation of smaller scintillation elements or fibers which allows for more scintillator material within a single scintillator pack or array. In further embodiments, the fibers may be grown to have uniform diameters but non-circular in cross-sectional shape or developed to have non-uniform diameters and non-circular cross-sections.

That shown in FIG. 6 illustrates a scintillator pack but may also illustrate a finished scintillator array. That is, the pack 86 shown in FIG. 6 may be cut or diced to form a scintillator array for a CT detector cell. In the embodiment having uniformity in fiber size throughout the pack, it is not critical that the pack be cut or diced at precise positions. That is, the entire pack is uniform; therefore, any section or portion cut away from the pack will also be uniform. As a result, the uniform packs 86 may be constructed and arbitrarily diced to match the dimensional requirements needed for a CT detector or other detector assembly. By fabricating uniform packs that may be cut or diced to form smaller and also uniform portions, a single manufacturing assembly or process may be developed whereupon the appropriately sized scintillator arrays are cut from the uniform pack rather than fabricating each of the differing sized arrays or packs separately and independently. This streamlining and consistency in the scintillator fabrication process reduces manufacturing costs, tooling, time, labor, and the like.

Still referring to FIG. 6, because each of the scintillator fibers 88 may be constructed to have a constant cross-sectional diameter and thereby create a uniformity throughout the scintillator pack 86, the alignment of the collimator assembly and the photodiode array to the resultant scintillator array is less critical. That is, unlike the photodiode, scintillator arrays developed from pack 86 are not pixilated. The non-pixelated orientation and layout of the scintillator fibers avoids alignment issues typically associated with the alignment of the photodiode to the scintillator array. Moreover, alignment concerns typically associated with the collimator assembly grid are also alleviated.

As stated above, the scintillator fibers may be ceramic fibers or single crystal fibers. Ceramic fibers are typically formed using an extrusion method with an organic binder. However, the burnout of the binder is usually very difficult and cracks in the structure can occur relatively easily. Further, the residue from the organic binder can cause serious deterioration of the performance of the scintillator that negatively affects light output, radiation damage resistance, and afterglow. Standard extrusion methods utilize an entire powder process whereupon each of the chemicals used to the form the scintillators are placed in powder form. However, the powder size greatly affects the density of the scintillator fiber and its sinter-ability. Accordingly, in accordance with one embodiment of the invention, a fabrication process for single ceramic fibers has been developed that is easy to control, avoids the drawbacks of separate powdering process typically associated with the extrusion.

Figure 7:
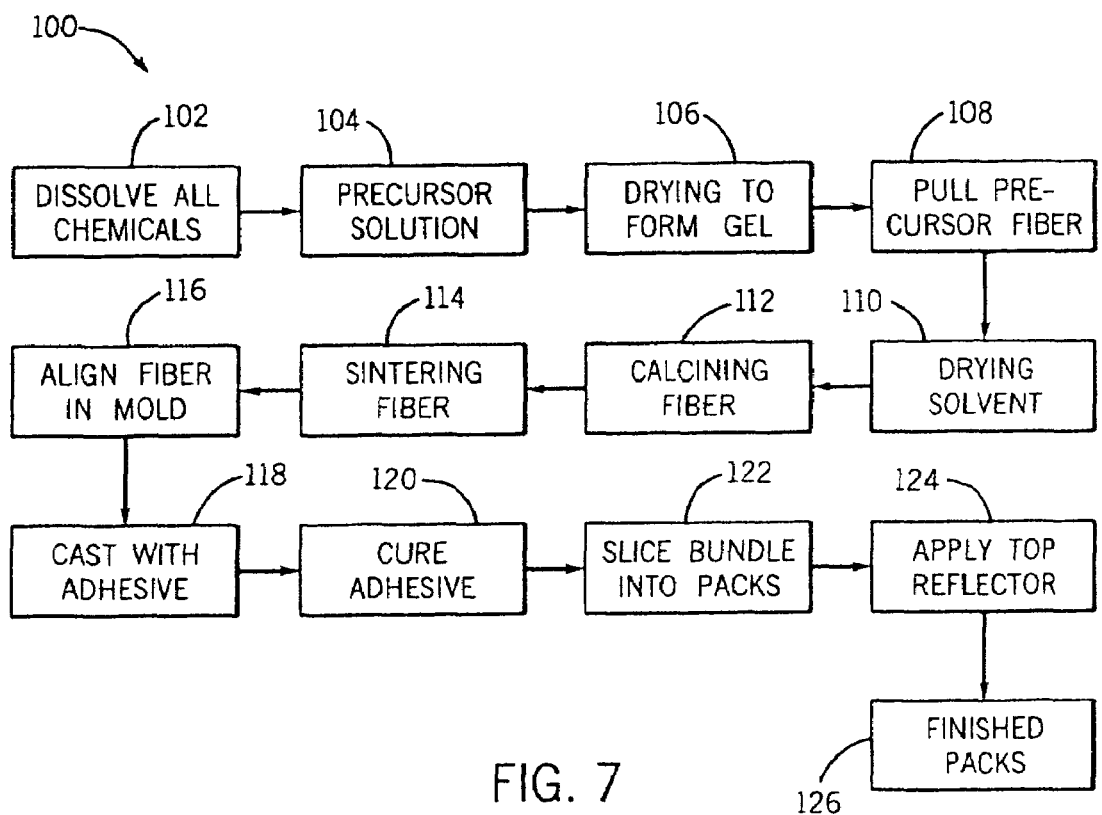
FIG. 7 is a flow chart setting forth the steps of one technique for fabricating the scintillator pack of FIG. 6.

Referring now to FIG. 7, a scintillator fabrication process map is shown. With this process or technique, the grain size of the created ceramic fiber is smaller than that typically provided by extrusion which yields pack density of close to 100 percent. The technique 100 begins at 102 with the dissolution of chemicals used to form a precursor solution at 104. The chemicals selected depend upon the type of scintillator system to be created. For example, in one system, the starting chemicals include lutetium acetate hydrate (>99.99%) $(Lu(O_2CCH_3)_3 \times H_2O)$, terbium acetate hydrate (>99.99%) $(Tb(O_2CCH_3)_3 \times H_2O)$, cerium nitrate (>99.99%) $(Ce(NO_3)_3 6H_2O)$, and aluminum formate hydrate (>99.99) $(Al(O_2CH)_3 3H_2O)$ with a proper ratio. For example, the proper ratio may be defined by the following stoichiometrical equation, $Lu_{0.8}Tb_{2.17}Ce_{0.03}Al_5O_{12}$. One skilled in the art would readily recognize that other composition ratios may be possible, such as those discussed in U.S. Ser. No. 10/316,151, now U.S. Pat. No. 6,793,848 B2, which is incorporated herein by reference and conunonly assigned to the Assignee of this application. The starting chemicals are then dissolved in hot distilled water 104 to form the precursor solution. Certain amounts of formic acid, ethylene glycol, and isobutyric acid are added to stabilize the solution. Alternately, the starting materials or chemicals are all nitrates. The nitrates are then dissolved in distilled water. Ethylene glycol and acetic acid or citric acid is then added to the dissolved solution.

Once the precursor solution is developed, the solution is heated 106 at about 60 to 80° C. to dry the water and increase the viscosity by polymerization. After sufficient drying, the solution becomes a translucent and, preferably, transparent gel with proper viscosity. From the gel, a precursor fiber is drawn from the gel at 108. The precursor fiber, as will described below, will form the basis for a plurality of ceramic scintillator fibers. The drawn or pulled fiber of gel material will be dried 110 in a drying oven at about 100 to 150° C. to dry up the solvent. The dried fiber will then be pulled into a temperature gradient furnace for calcining at 112. The first stage in the furnace is pyrolysis at about 400° C. to 1100° C. The fiber will be converted into a ceramic phase of garnet structure.

Once the ceramic fiber is formed, the fiber will undergo a sintering stage at 114 with a temperature between 1650 and 1775° C. and, preferably, about 1700° C. for full densification and desired grain growth. The final stage performed in the furnace is thermal annealing. It should be noted that the pyrolysis, sintering, and annealing steps may be done in three separate furnaces for atmospheric control. The final and annealed fiber will then be cut resulting in plurality of uniformly shaped ceramic scintillator fibers. Generally, the fibers will be 1-10 μm in size. The fibers are then aligned in a mold at 116. The mold is designed to closely pack and align each of the fibers in parallel with one another. The mold also dimensionally defines the resulting scintillator pack. The bundle of scintillator fibers are then cast with an adhesive material loaded with reflector material 118, such as titanium oxide ($TiO_2$). The reflector material is a radiation resistant epoxy with low viscosity. Because the fibers are closely aligned within the mold, the voids between each fiber are minute. These very small voids, however, are filled with reflector material used to improve light emissions toward the photodiode array and reduce cross talk between adjacent scintillator fibers.

Following casting of the fiber bundle with adhesive, the bundle is cured at 120 to form a scintillator pack of reflective coated scintillator fibers. The cure pack is then sliced at 122 to form a number of scintillator arrays having uniformly aligned scintillator fibers. Preferably, the pack is sliced along lines perpendicular to the fibers' longitudinal axis. A layer of optically reflective material, such as reflector tape, is then coated on one surface of each scintillator array at 124. The surface may also be polished and the sputter coated with reflective material such as aluminum, silver, gold, and the like. Following application of the optically reflective layer, if any, a number of uniformly sized scintillator arrays or packs result and the process ends at 126.

In another embodiment, the starting materials or chemicals used to develop the precursor solution include $Y_2O_3$, $Gd_2O_3$, $Eu_2O_3$ (all >99.99%), and $Pr(NO_3)_3\cdot xH_2O$ (>99.99%). With this embodiment, the oxides of desired ratio will be mixed together and dissolved in nitric acid. Then the praseodymium nitrate will be added into the solution. A certain amount of ethylene glycol and nitric acid will be added to make a transparent solution. The solution will be heated at about 60-80° C. for polymerization. Once the solution becomes a transparent gel and the viscosity is suitable, a fiber will be drawn from the gel. The rest of the fabrication process will be similar to that described above with respect to the Lu—Tb—Al—O—Ce system, only the temperature and atmosphere will be different. One example of the composition in accordance with this system is

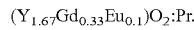

Figure 8:
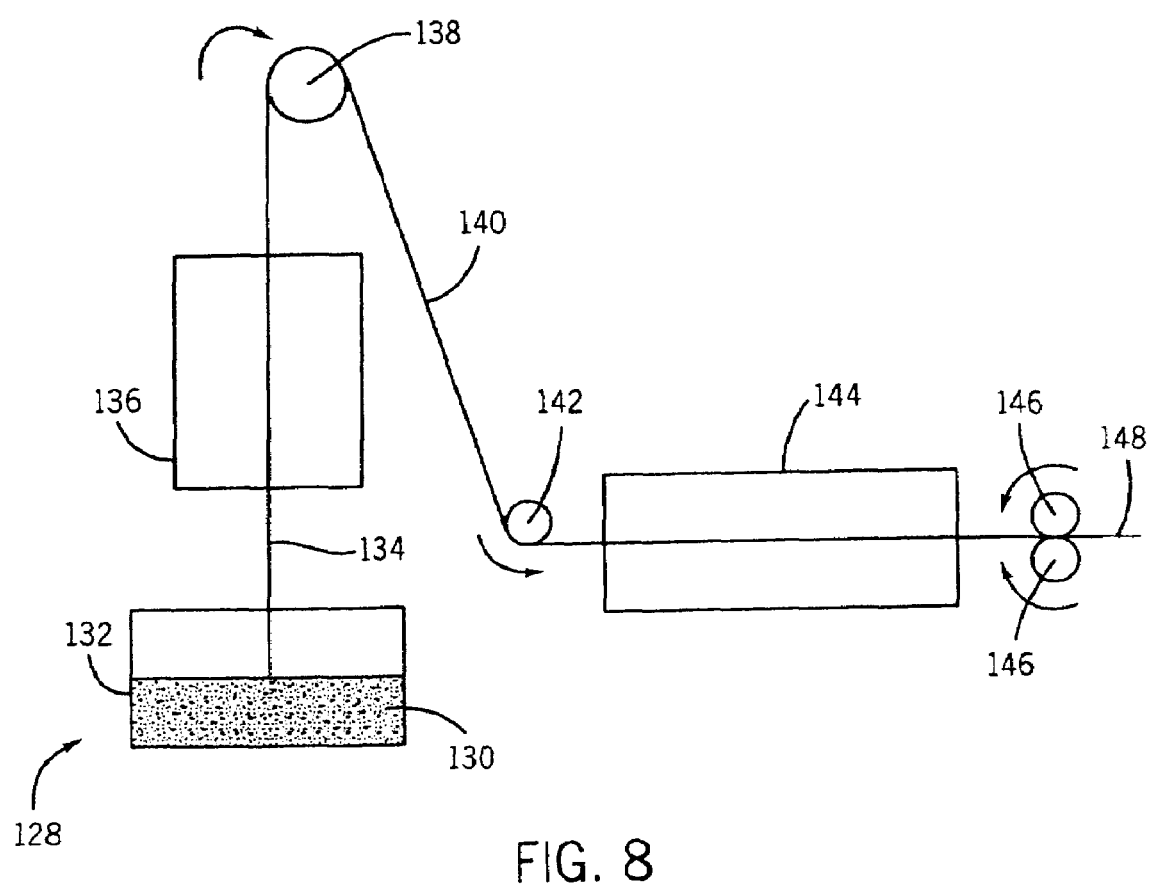
FIG. 8 is a schematic representation of an apparatus capable of implementing the technique of FIG. 7.

Shown in FIG. 8 is a system for implementation the fiber growth steps detailed above with respect to FIG. 7. System 128 includes a crucible 132 or other container capable of housing the aforementioned starting materials and the dissolution of the starting materials into a precursor solution 130. The crucible is then heated by a heater (not shown) to develop a precursor gel within the crucible. A precursor fiber 134 is then pulled or drawn from the gel and input into a drying oven 136. The precursor fiber 134 is pulled into the drying oven by pulling agent 138. The dried fiber 140 is then input by pulling agent 142 into a calcining and sintering oven 144. Upon sintering and annealing of fiber 140, pulling agents 146 remove the annealed fiber 148 from the sintering oven 144. As discussed above, the annealed fiber or rod is then diced to form a plurality of scintillator fibers used to form a scintillator array.

The present invention also contemplates a plurality of single crystal fibers developed to form a scintillator array from a crystallization system with garnet as the crystal phase. Each of the single crystal fibers operates as a scintillation element and is constructed to direct light out to a photodiode or other light detection element. Similar to the ceramic fibers previously described, the single crystal fibers may be aligned in parallel and bundled together to form a scintillator pack or array similar to that shown in FIG. 6. Moreover, the single crystal fibers may have a uniform or common cross-sectional diameter whereupon the resulting scintillator pack would be uniform. Alternately, the fibers of different cross-sectional diameters may be grown and combined into a single scintillator pack to maximize pack density and dose efficiency. In the embodiment illustrated in FIG. 6, each of the fibers has a circular cross-section; however, other cross-sectional shapes are contemplated and within the scope of the invention.

Single crystal fiber is highly transparent and has very low impurity. This transparency improves the light collection efficiency of the corresponding photodiode array. Moreover, because the crystallization process is a purification process that can expel many undesirable impurities, afterglow of each crystal fiber may be minimized. In one embodiment, the single crystal fiber scintillator is composed of $(Lu_xTb_{1-x-y}Ce_y)_3Al_5O_{12}$ (LuTAG). "X" ranges from 0.5 to 1.5 and "y" ranges from 0.01 to 0.15. Due to the incongruent melting of $Tb_3Al_5O_{12}$, Lu is added to stabilize the garnet structure. Ce is added as the scintillation activator. The garnet phase is essential for transparent single crystal fibers. Further, operating at a congruent melting composition is preferred for growing crack-resistant fibers.

Figure 9:
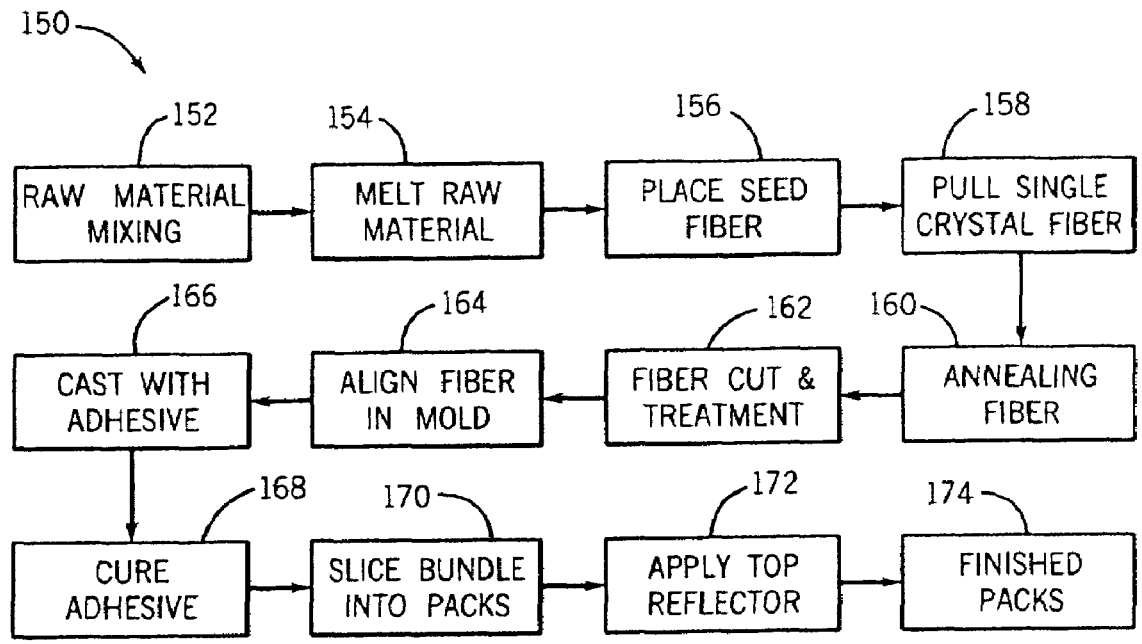
FIG. 9 is a flow chart setting forth the steps of another technique for fabricating the scintillator pack of FIG. 6.

Referring now to FIG. 9, a process map or steps of a technique for developing a scintillator pack comprised of single crystal fibers is shown. The technique 150 begins at 152 with the mixing of raw materials used as a base for scintillator crystal growth. In one embodiment, the raw materials include $Tb_4O_7$ (>99.99%), $Lu_2O_3$ (>99.99%), $Al_2O_3$ (>99.99%), and $CeO_2$ (>99.99%). The powder oxides are mixed by a ball mill with alcohol or distilled water and then dried at 152. The mixture is then melted at 154 in a molybdenum or iridium crucible at about 1800 to 1900° C. Stirring is used to homogenize the melt. Once the melt is homogenized, a seed fiber is placed in the melt at 156. From the seed fiber, a single crystal rod or fiber is pulled at 158. The pulled fiber then undergoes annealing at 160 at a prescribed temperature, i.e. 1500° C. Following annealing, the rod of single crystal scintillator material is cut or diced at 162. The cutting at 162 parcels the single rod of scintillator material into a number of single crystal fibers having a common and uniform diameter. Preferably, each of the fibers will have a common length.

The resulting fibers are then aligned in a mold at 164. The mold dimensionally defines the scintillator pack to be formed from the single crystal fibers and also operates to closely pack the fibers. To increase the number of fibers within the mold, some fibers of different cross-sectional diameters may be used. As noted above, increasing the number of scintillation elements within a scintillator array increases the quantum detection efficiency (QDE) of the scintillator array. At 166, the aligned fibers are cast with a reflective adhesive material used to mechanically bond the fibers to one another into a single structure or assembly. The adhesive material mechanically bonds adjacent fibers to one another but may also be doped with a reflective material such as $TiO_2$ to reduce cross-talk emissions between the scintillation elements. The bundle of cast fibers is then cured at 168 and subsequently diced at 170 to form a number of scintillator packs 170. Preferably, the pack is sliced along lines perpendicular to the fibers" longitudinal axis. A layer of optically reflective material, such as reflector tape, is then coated on one surface of each scintillator array at 172. The surface may also be polished and the sputter coated with reflective material such as aluminum, silver, gold, and the like. Following application of the optically reflective layer, if any, a number of uniformly sized scintillator arrays or packs result and the process ends at 174. If the fibers' were grown to be uniform in size and shape, then the array of each of the resulting packs will also be uniform in size shape.

Figure 10:
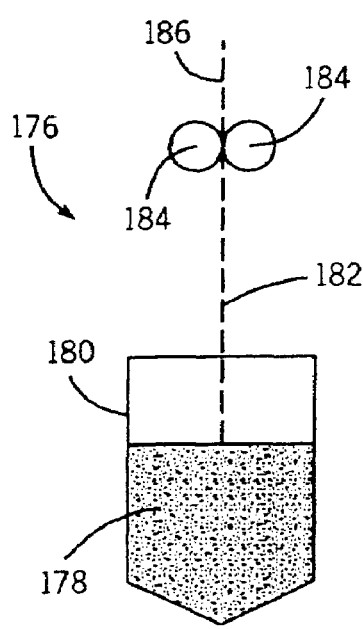
FIG. 10 is a schematic illustrating one apparatus for carrying out the steps of FIG. 9.
Figure 11:
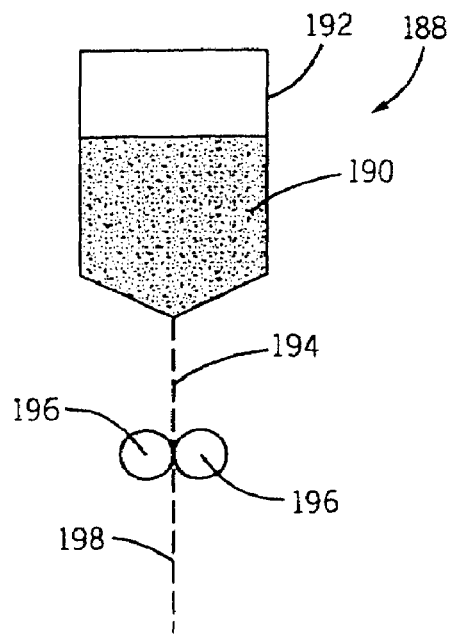
FIG. 11 is a schematic illustrating another apparatus for carrying out the steps of FIG. 9.

Referring now to FIGS. 10 and 11, a number of methods are contemplated to pull the crystal fiber from the melt. One method is pulling up, similar to the well-known Czochralski method 176 illustrated in FIG. 10. Another method is a pulling down method such as that shown in FIG. 11. For the pulling up method or technique of FIG. 10, the starting materials 178 are mixed in a crucible 180. A seed fiber is placed in the crucible and is used for crystal growth. The seed fiber has a known crystal orientation (normally {111} direction). From the seed fiber, a crystal rod or fiber 182 is pulled using pulling agents 184. The pulled fiber 186 may then be processed (i.e. heated, sintered, annealed, and the like) in accordance with the Czochralski method.

For the pulling down method 188 schematically shown in FIG. 11, the starting materials 190 are placed in a crucible 192 having an orifice machined at the bottom thereof. The orifice has a diameter of about 0.2 to 0.8 mm depending on the desired fiber diameter. The pulling rate is about 1-10 mim/minutes. A seed fiber is used to start the crystal growth. The seed fiber has a known crystal orientation (normally {111} direction). The crucible 192 is first heated to about 50 to 100° C. above the melting temperature of the composition, then the temperature is decreased to about 20° C. above the melting temperature and maintained at that level. The seed fiber is then inserted into the melt slowly. When a small part of the seed (normally a few mm are in the melt), the pulling starts. The crystal growth 194 is pulled by agents 196 under Argon atmosphere to prevent the oxidation of the crucible 192. The resultant fiber 198 is then cut into a certain length and annealed in a controlled atmosphere [normally Argon with certain oxygen ($O_2$) partial pressure]. The annealing temperature is around 1500° C.

Figure 12:
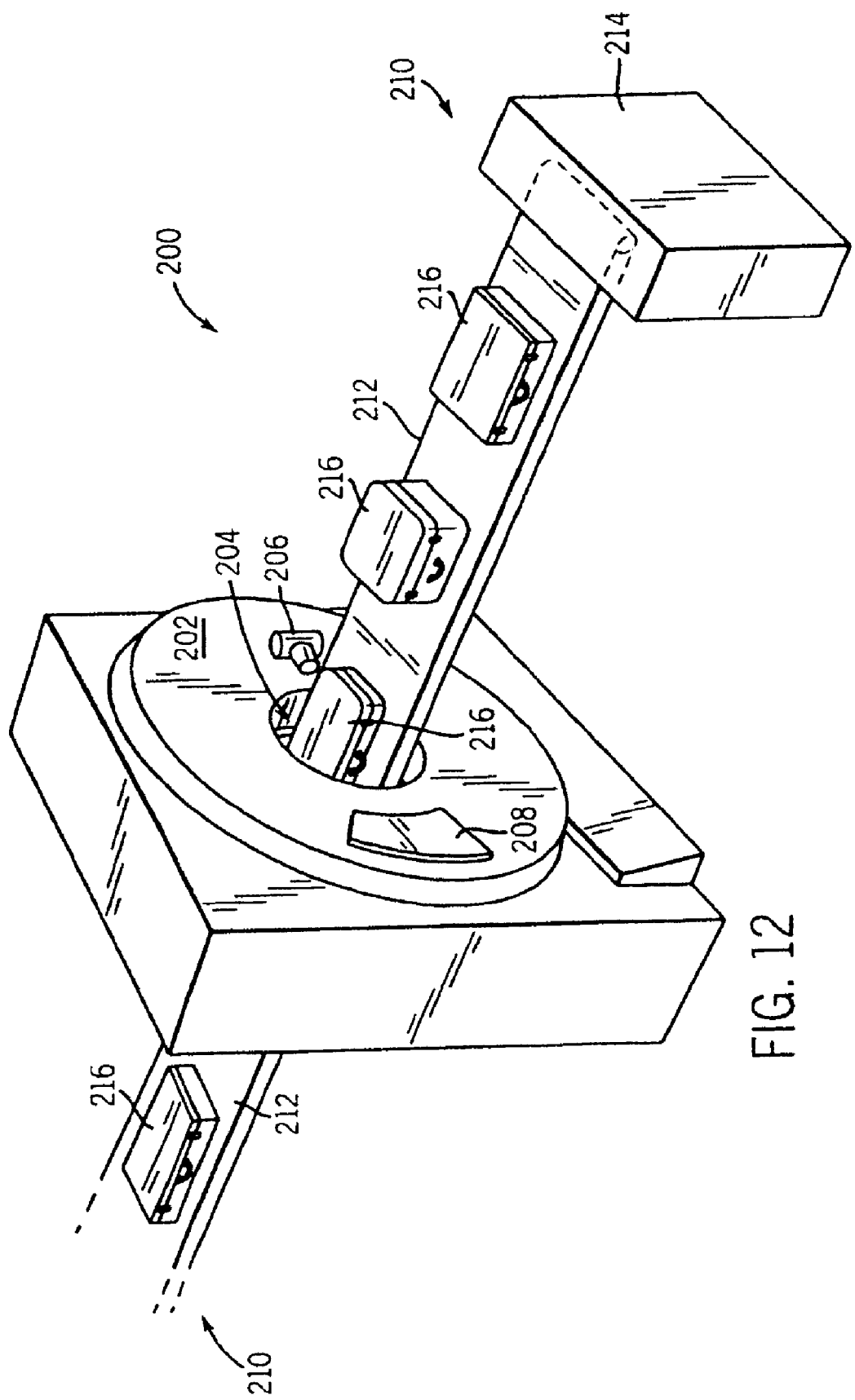
FIG. 12 is a pictorial view of a CT system for use with a non-invasive package inspection system.

Referring now to FIG. 12 package/baggage inspection system 200 includes a rotatable gantry 202 having an opening 204 therein through which packages or pieces of baggage 216 may pass. The rotatable gantry 202 houses a high frequency electromagnetic energy source 206 as well as a detector assembly 208 having scintillator arrays comprised of scintillator cells similar to that shown in FIG. 6. A conveyor system 210 is also provided and includes a conveyor belt 212 supported by structure 214 to automatically and continuously pass packages or baggage pieces through opening to be scanned. Objects are fed through opening by conveyor belt 212, imaging data is then acquired, and the conveyor belt 212 removes the packages 216 from opening 204 in a controlled and continuous manner. As a result, postal inspectors, baggage handlers, and other security personnel may non-invasively inspect the contents of packages 216 for explosives, knives, guns, contraband, etc.

Therefore, in accordance with one embodiment of the present invention, a CT detector array includes a plurality of collimator elements configured to collimate x-rays projected thereat as well as a non-pixelated scintillator pack formed of a material that illuminates upon reception of x-rays. The CT detector array further includes a photodiode array optically coupled to the non-pixelated scintillator pack and configured to detect illumination from the scintillator pack and output electrical signals responsive thereto.

In accordance with another embodiment of the present invention, a CT detector array comprising a non-pixelated array of scintillation elements configured to illuminate upon the reception of high frequency electromagnetic energy and coupled to an array of light detection elements configured to detect illumination of the array of scintillation elements and output a plurality of electrical signals generally indicative of high frequency electromagnetic energy received by the array of scintillation elements is provided. The detector array is formed by developing the plurality of single crystal fibers of scintillation material and casting the plurality of crystal fibers with an adhesive material. The detector array is further formed by curing the plurality of crystal fibers in adhesive material to form a cured pack and cuffing the cured pack to a specified dimension.

According to another embodiment of the present invention, a method of manufacturing a CT detector array having a non-pixelated scintillator array includes the steps of developing a material base from which scintillators may be grown and pulling a rod of scintillating material from a material base. The method further includes cuffing the rod to form a plurality of scintillator fibers and aligning the plurality of scintillator fibers into a scintillator bundle. The scintillator bundle is then sliced into a number of scintillator packs whereupon a reflector coating is applied to the number of scintillator packs.

The present invention has been described in terms of the preferred embodiment, and it is recognized that equivalents, alternatives, and modifications, aside from those expressly stated, are possible and within the scope of the appending claims.

What is claimed is:

1. A method of manufacturing a CT detector array having a non-pixelated scintillator array, the method comprising the steps of:

developing a material base from which scintillators may be grown;

pulling a rod of scintillator material from the material base;

cutting the rod to form a plurality of scintillator fibers;

aligning the plurality of scintillator fibers into a scintillator bundle;

slicing the scintillator bundle into a number of scintillator packs; and applying a reflector coating to the number of scintillator packs.

2. The method of claim 1 wherein the step of developing a material base includes the steps of:
dissolving a number of chemicals to form a precursor solution; and
heating the precursor solution to form a transparent gel.

3. The method of claim 2 further comprising the steps of:
heating the pulled rod of scintillator material;
calcining the rod;
sintering the rod; and
annealing the sintered rod.

4. The method of claim 3 further comprising the step of converting the rod into a ceramic phase having a garnet structure prior to the sintering step.

5. The method of claim 3 wherein the step of developing a material base includes the steps of:
mixing a number of powder oxides with a ball mill and a dissolving solution;
drying the dissolved solution;
melting the dissolved solution; and
homogenizing the dissolved solution.

6. The method of claim 5 wherein the number of powder oxides includes $Tb_4O_7$, $Lu_2O_3$, $Al_2O_3$, and $Ce_2O_3$ and the dissolving solution includes alcohol.

7. The method of claim 5 wherein the step of pulling includes the steps of:
growing a seed fiber in the homogenized solution; and
pulling the seed fiber downward to develop the rod of scintillator material.

8. The method of claim 5 further comprising the step of optically coupling the scintillator packs to a photodiode array configured to detect illumination from the scintillator pack and output electrical signals responsive thereto, the photodiode array having a plurality of photodiodes.

9. The method of claim 8 wherein the coupling further comprises aligning each photodiode with a single respective scintillator pack to detect light from the scintillator fibers therein.

10. The method of claim 2 wherein the number of chemicals includes lutetium acetate hydrate, terbium acetate hydrate, cerium nitrate, and aluminum formate hydrate.

11. The method of claim 2 wherein the number of chemicals includes $Y_2O_3$, $Gd_2O_3$, $Eu_2O_3$, and $Pr(NO_3)_3 \times H_2O$.

12. A method for constructing a non-pixelated scintillator array comprising the steps of:
developing a plurality of single crystal fibers of scintillation material;
casting the plurality of single crystal fibers with an adhesive material;
curing the plurality of single crystal fibers and adhesive material to form a cured pack of a first dimension;
cutting the cured pack to a specified dimension that is different from the first dimension; and
wherein the plurality of crystal fibers has a uniform cross-sectional diameter.

13. The method of claim 12 wherein the step of developing further includes the step of growing the plurality of single crystal fibers from a mixture of $Tb_4O_7$, $Lu_2O_3$, $Al_2O_3$ and $CeO_2$.

14. The method of claim 13 wherein the step of growing further comprises:
incorporating one of distilled water and alcohol into the mixture;
allowing the mixture to dry; and
melting and homogenizing the dried mixture.

15. The method of claim 14 further comprising the step of pulling crystal fibers from the homogenized mixture.

16. The method of claim 12 further comprising the step of coating a layer of reflective material to one end surface of the cured pack.

17. The method of claim 12 further comprising the step of sputter coating reflective metal on one end surface of the cured pack.

18. The method of claim 12 further comprising the step of depositing adhesive material in any voids existing between adjacent crystal fibers.

19. A method of manufacturing a CT detector array comprising the steps of:
preparing a material base from which scintillators may be grown;
pulling a rod of scintillator material from the material base;
cutting the rod to form a plurality of scintillator fibers;
aligning the plurality of scintillator fibers into a scintillator bundle;
slicing the scintillator bundle into a number of scintillator packs;
applying a reflector coating to the number of scintillator packs;
optically coupling one of the scintillator packs to a single light detection element configured to detect illumination of the scintillator pack and output electrical signals generally indicative of high frequency electromagnetic energy received by the scintillator pack.

20. The method of claim 19 further comprising the steps of:
heating the pulled rod of scintillator material;
calcining the rod;
sintering the rod; and
annealing the sintered rod.

* * * * *